United States Patent
Jung

[11] Patent Number: 5,830,167
[45] Date of Patent: Nov. 3, 1998

[54] SPLINT FOR A PERSON WITH A FRACTURED BONE OR INTERVERTEBRAL HERNIATED DISK

[76] Inventor: Hyo Sik Jung, No. 506 Samik Plaza, 706 1-da samchun-dong, Wansan-ku, Jeonju-si, Jeonlanam-do, Rep. of Korea

[21] Appl. No.: 715,827

[22] Filed: Sep. 19, 1996

[51] Int. Cl.$^6$ ........................................... A01F 5/00
[52] U.S. Cl. ............................................. 602/19
[58] Field of Search ................. 602/5–8, 19, 20, 602/23, 18

[56] References Cited

U.S. PATENT DOCUMENTS

| | | | |
|---|---|---|---|
| 3,307,535 | 3/1967 | Locke | 602/19 |
| 3,434,469 | 3/1969 | Swift | 602/19 |
| 3,717,143 | 2/1973 | Johnson | 602/19 |
| 4,169,469 | 10/1979 | Arluck | 602/7 |
| 4,475,543 | 10/1984 | Brooks et al. | 602/19 |
| 4,572,167 | 2/1986 | Brunswick | 602/19 |
| 5,111,806 | 5/1992 | Travis | 602/19 |
| 5,147,261 | 9/1992 | Smith et al. | 602/19 X |
| 5,179,942 | 1/1993 | Drulias et al. | 602/19 X |
| 5,366,438 | 11/1994 | Martin, Sr. | 602/18 X |
| 5,387,183 | 2/1995 | Jones | 602/19 |
| 5,388,274 | 2/1995 | Glover et al. | 602/19 X |
| 5,433,697 | 7/1995 | Cox | 602/19 |
| 5,503,620 | 4/1996 | Danzger | 602/19 |
| 5,547,462 | 8/1996 | Lanigan et al. | 602/19 |

*Primary Examiner*—Linda C.M. Dvorak
*Attorney, Agent, or Firm*—Lynn Fiorito Watts

[57] ABSTRACT

A splint, used as a support for a broken bone or herniated intervertebral disk so that the bone or disk stays in a particular position while it heals, is disclosed. The splint includes a panel, which is formed of a material capable of being softened at temperatures of about 70°C.–90°C. and has a plurality of bending slits. Due to the slits, the splint is not only appropriately shaped into a configuration agreeable to the contour of an affected part of the body, it is also free of any rumples while being put on the affected part of the body. In the splint, the parts of the panel which will be brought into contact with a patient's skin are lined with sponge and soft cloth suitable to protect the skin and give a soft and delightful sensation to a patient. The panel is covered with an outer cover which allows the splint to be easily put on or removed from the affected part particularly when the splint is put on a person with a herniated disk.

1 Claim, 9 Drawing Sheets

SPLINT FOR A PERSON WITH A FRACTURED BONE OR INTERVERTEBRAL HERNIATED DISK

BACKGROUND OF THE INVENTION

1. Field of the Invention

The present invention relates, in general, to splints used as medical supports for broken bones or herniated intervertebral disks of persons having a fractured bone or intervertebral herniated disk so that the bones or disks stay in their particular positions while they heal and, more particularly, to a structural improvement in such splints for appropriately shaping a splint into a configuration corresponding to the contour of an affected part of the body. The above structural improvement is also for protecting the patient's skin, giving a soft and delightful sensation to a patient, and allowing the splint to be easily put on or removed from the affected part of the body particularly when using the splint for a person with an intervertebral herniated disk.

2. Description of the Prior Art

In the prior art, several types of plaster casts or splints have been used to immobilize an affected part of the body of a person with a fractured bone or intervertebral herniated disk so that the broken bone or herniated intervertebral disk stays in a particular position while it heals. Hereinbelow, the term "intervertebral disk" will be referred to simply as "disk".

In order to put a person with a fractured bone or herniated disk in a typical plaster cast, a plaster bandage impregnated with plaster paste is put on an affected part of the patient and in turn becomes hard as the plaster paste dries. The advantage of the typical plaster cast resides in that it is easily shaped into a configuration agreeable to the contour of the affected part of the body and is not expensive. However, the typical cast has problems in that the cast takes too long as the plaster bandage becomes hard, and the cast cannot be reused. The cast is substantially heavy enough to disturb the movement of the patient and allows poor air circulation around the affected part thereby causing the patient to itch around the affected part.

The plaster cast also poorly transmits X-rays, so that it is impossible to X-ray an affected part of the body in the cast in order to precisely check the healing condition of a broken bone or herniated disk of a patient. Another problem of the plaster cast is caused by a motor-driven plaster saw which is typically used for removing the cast from the affected part of the body when the broken bone or herniated disk has completely healed. That is, the plaster saw not only generates gypsum dusts and operational noises upsetting the patient as well as the operating surgeon, it also strikes the patient with terror while removing the cast.

In an effort to overcome the above problems caused by the typical plaster casts, Korean Patent Laid-open Publication No. 91-5831 proposed a reusable splint, which is made of a material including a vinyl chloride copolymer with vinylacetate as its ingredient and which is used to immobilize an affected part of the body. The above Korean splint is easily put on the affected part of the body as it is softened at temperatures of 70° C.–90° C. and becomes hard within 5 minutes at a normal room temperature. Another advantage of the above Korean splint resides in that it is reusable after it is softened again at the predetermined temperatures, and it has a detachable construction.

However, the above splint has problems in that it gives a bad sensation to a patient due to its material and becomes rumpled at portions corresponding to bending parts of the body. Another problem of the above splint resides in that it is difficult to put the splint on an affected part of a patient with a herniated disk.

SUMMARY OF THE INVENTION

It is, therefore, an object of the present invention to provide a splint for persons with a fractured bone or herniated disk wherein the above problems can be overcome, and to provide a splint which is formed by providing a plurality of slits on each panel of the above Korean splint so that the splint not only is appropriately shaped into a configuration agreeable to the contour of an affected part of the body but also is free from any rumples.

Another object of the present invention is to provide a splint for persons with a fractured bone or herniated disk wherein the parts to be brought into contact with a patient's skin are lined with a soft material suitable to protect the skin and give a soft and delightful sensation to the patient.

A further object of the present invention is to provide a splint for persons with a fractured bone or herniated disk which has an outer cover that allows the splint to be easily put on or removed from the affected part particularly when the splint is put on a person with a herniated disk.

In order to accomplish the above objects, a splint according to an embodiment of the present invention comprises a panel, which is formed of a material capable of being softened at temperatures of about 70° C.–90° C. The above panel is lined with both a sponge and a soft cloth and is covered with an outer cover. The panel also has a plurality of bending slits, which allow the panel to be easily shaped into a configuration agreeable to the contour of an affected part of the body without forming any rumples. The outer cover of the splint has a detachable construction, so that the splint of this invention may be easily removed from the affected part of the body.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
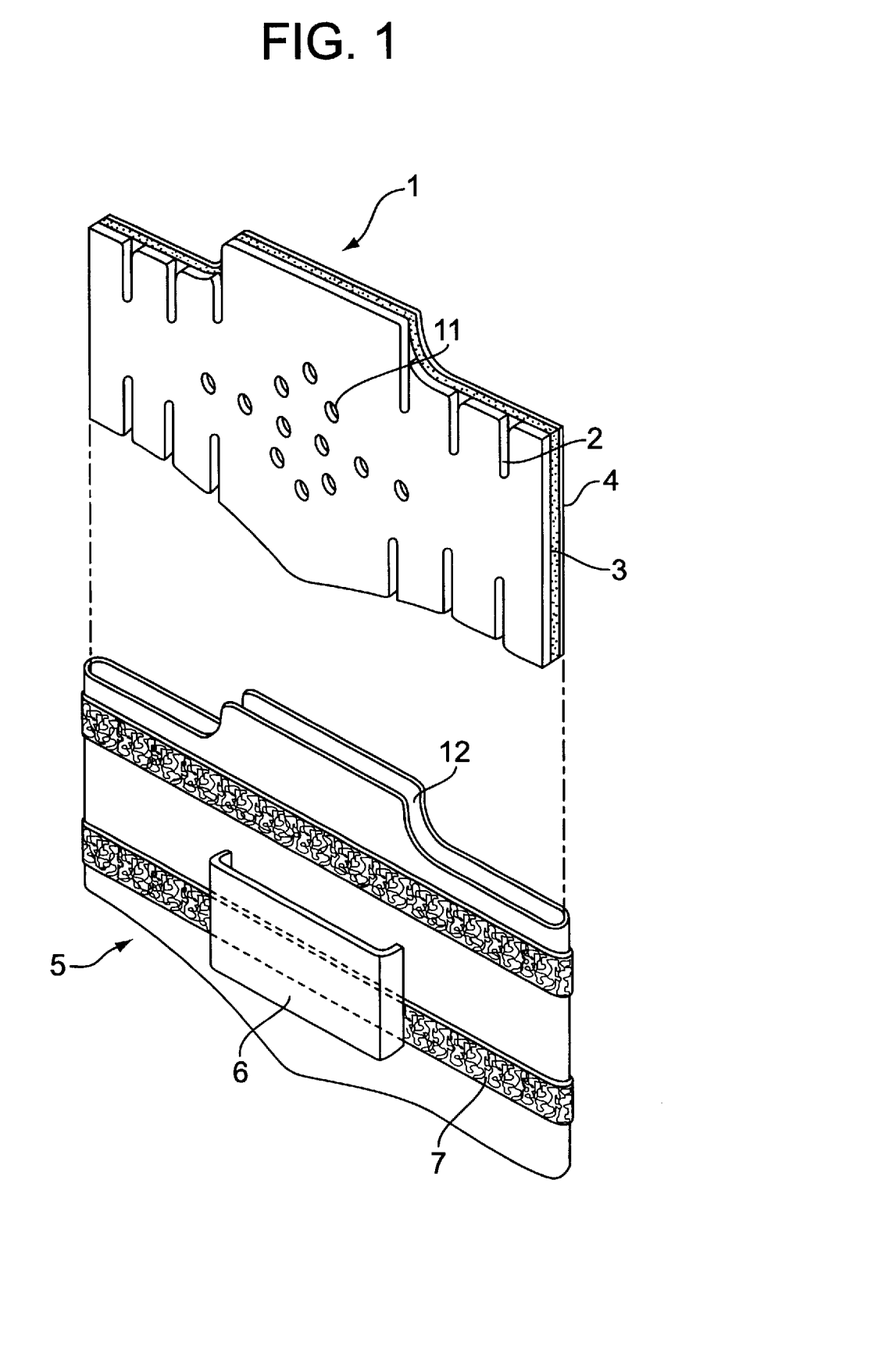
FIG. 1 is an exploded perspective view showing the configuration and construction of the front panel of a jacket-type splint for persons with a herniated disk in accordance with the primary embodiment of the present invention.
Figure 2:
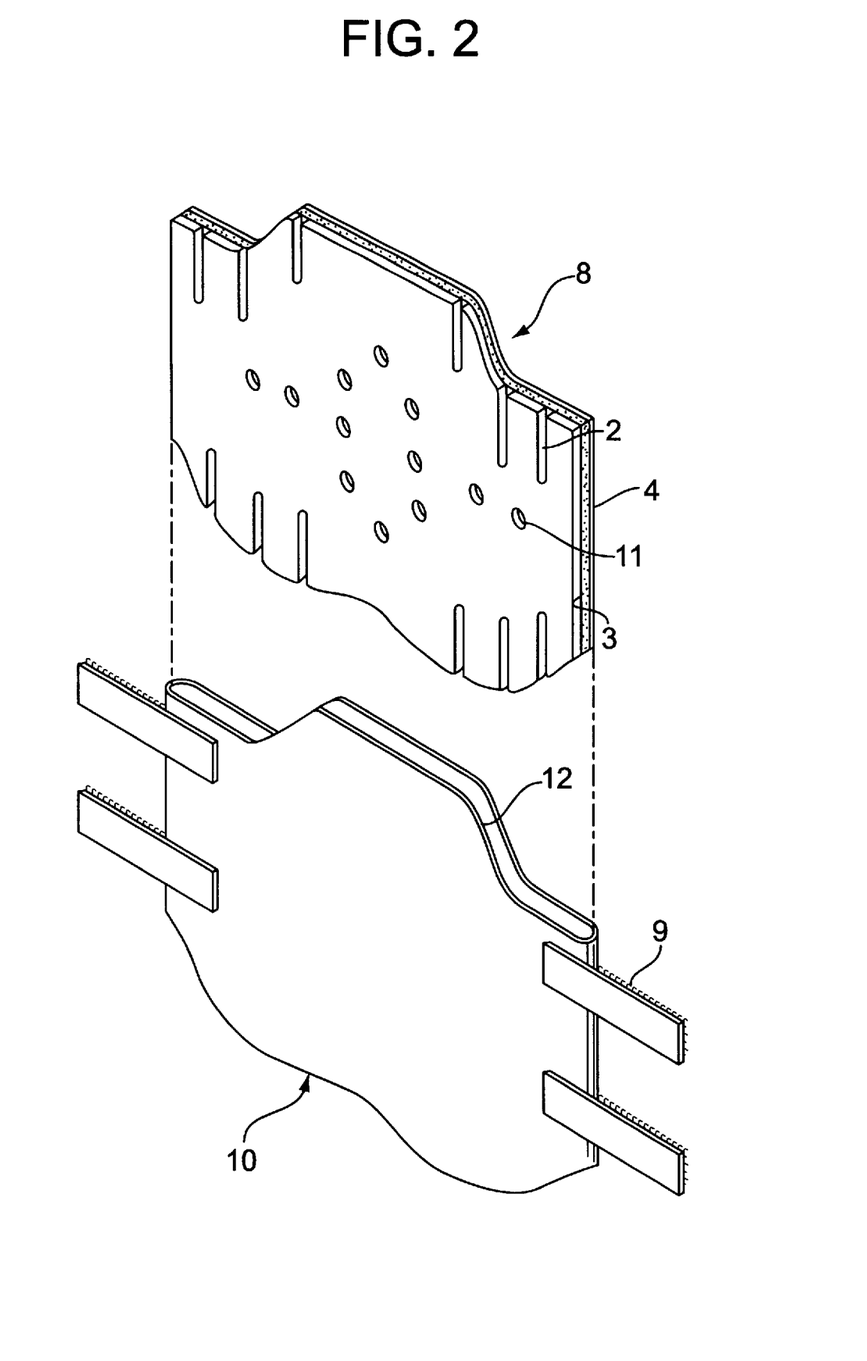
FIG. 2 is an exploded rear perspective view showing the configuration and construction of the back panel of the jacket-type splint for persons with a herniated disk according to the primary embodiment of this invention.
Figure 3:
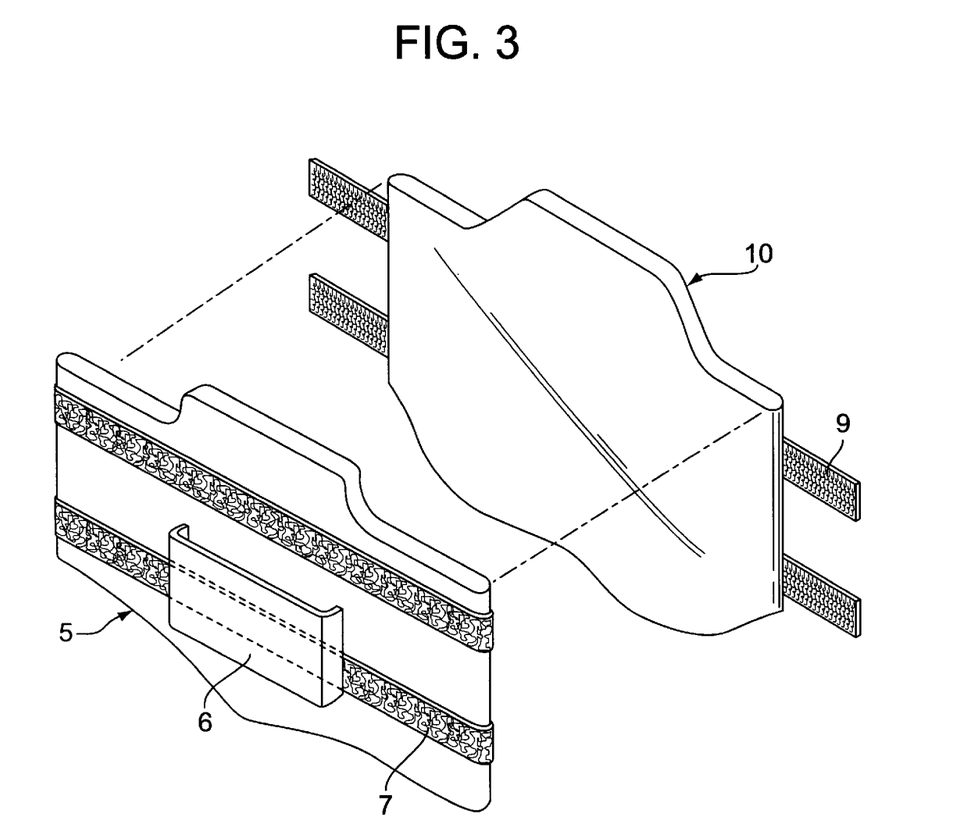
FIG. 3 is a perspective view showing the configuration and construction of the jacket-type splint for persons with a herniated disk according to the primary embodiment of this invention.

FIGS. 1 to 3 show the configuration and construction of a jacket-type splint for persons with a herniated disk in accordance with the primary embodiment of the present invention.

As shown in FIGS. 1 to 3, the jacket-type splint comprises front and back panels 1 and 8, each of which is formed of a known material capable of being softened at temperatures of about 70° C.–90° C. Such a known material may be one comprising a vinyl chloride copolymer with vinylacetate as an ingredient as described in Korean Patent Laid-Open Publication No. 91-5831, to Hyo Sik Jung, entitled "Making Method of a Material of an Aid for a Person with an Intervertebral Herniated Disk and the Aid", published Apr. 27, 1991, and which is incorporated herein by reference. Each panel 1, 8 is provided with a plurality of bending slits 2, which allow each panel to be easily shaped into a configuration agreeable to the contour of an affected part of the body. Each panel 1, 8 is also lined with both a sponge 3 and a soft cloth 4. In this case, the sponge 3 is layered on the inside wall of each panel 1, 8, while the cloth 4 is layered on the sponge 3. The panels 1 and 8 are also covered with outer covers 5 and 10, respectively, prior to sewing the edge of each cover 5, 10. The outer cover 5 of the front panel 1 has a pocket 6. Two VELCRO rough strips 7 are longitudinally mounted to the front panel's outer cover 5, while four VELCRO hook strips 9 are mounted to both side edges of the back panel's outer cover 10.

In FIGS. 1 to 3, the reference numeral 11 denotes air ventilation holes formed on each panel 1, 8, and the numeral 12 denotes an opening of each cover 5, 10 for receiving an associated panel 1, 8 prior to sewing the edge of each cover.

As described in detail, the front panel 1 is provided with the bending slits 2 and is lined with the sponge 3 and soft cloth 4 through bonding. The slits 2, which are vertically formed on the top and bottom edges of the panel 1, allow the panel 1 to be easily shaped into a configuration agreeable to the contour of an affected part of the body while preventing rumples from forming on the panel 1. The sponge 3 and cloth 4 are lined on the inside wall of the panel 1, which is brought into contact with the patient's skin, thereby giving a soft and delightful sensation to the patient.

The air ventilation holes 11 allow air to pass therethrough thus providing good air circulation around the affected part of the body wearing the splint. In the present invention, the holes 11 are not formed on either the sponge 3 or the cloth 4.

As shown in FIG. 1, the front panel 1 is inserted into the cover 5 through the opening 12 prior to sewing the edge of the cover 5. The panel 1 with the cover 5 is, thereafter, put on the abdomen of a patient and is shaped into a configuration corresponding to the contour of the abdomen while heating the panel 1. The covered panel 1 is thus brought into close contact with the patient's abdomen.

In the present invention, the sponge 3, cloth 4, VELCRO fasteners 7 and outer cover 5 must be made of materials resisting heat of not less than 100° C.

The outer cover 5 is formed of a soft and durable cloth. The pocket 6 of the cover 5 allows a patient to carry one's necessaries.

The VELCRO rough strips 7 mounted to the front panel's cover 5 stick to the VELCRO hook strips 9 of the back panel's cover 10 when pressed, thus coupling the covered panels 1 and 8 together. Of course, it should be understood that the VELCRO hook strips may be mounted to the back panel's cover 10, while the VELCRO rough strips may be mounted to the front panel's cover 5.

The back panel 8 with the cover 10 has the construction similar to the above-mentioned front panel 1. The difference between the two covered panels 1 and 8 resides in the configuration of the VELCRO strips mounted thereto. That is, the two longitudinal VELCRO rough strips 7 are mounted to the front panel's cover 5, while the four short VELCRO hook strips 9 are mounted to both side edges of the back panel's cover 10.

In the same manner as described for the covered front panel 1, the back panel 8 with the cover 10 is put on the back of the patient and is shaped into a configuration corresponding to the contour of the back while heating the panel 1 at temperatures of about 70° C.–90° C. That is, after putting the covered front panel 1 on the abdomen of the patient by bending both side edges of the panel 1 rearward, the covered back panel 8 is put on the back of the patient. In this case, both side edges of the back panel 8 are bent forward so as to overlap the bent edges of the panel 1, respectively. Thereafter, the VELCRO strips 9 of the cover 10 are pressed onto the VELCRO strips 7 of the cover 5, so that the strips 7 and 9 stick together thereby coupling the covered panels 1 and 5 together.

Figure 4:
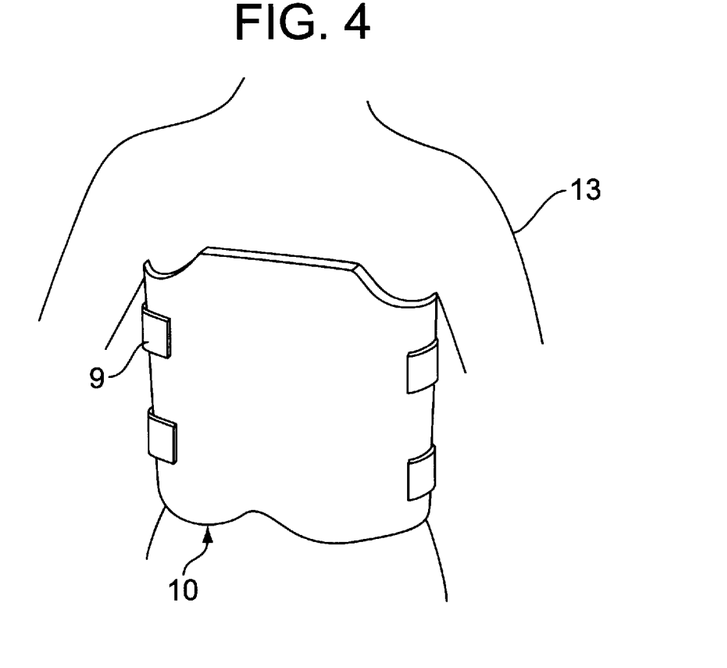
FIG. 4 is a rear perspective view showing the operational effect of the above splint put on a person with a herniated disk.
Figure 5:
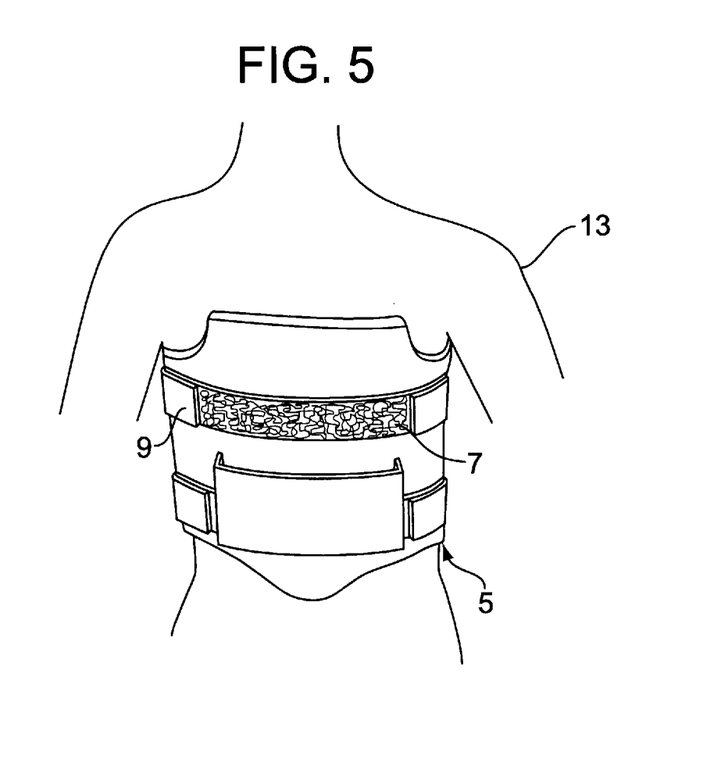
FIG. 5 is a front perspective view showing the operational effect of the above splint put on a person with a herniated disk.

FIGS. 4 and 5 show the operational effect of the above jacket-type splint put on a person with a herniated disk.

Figure 6:
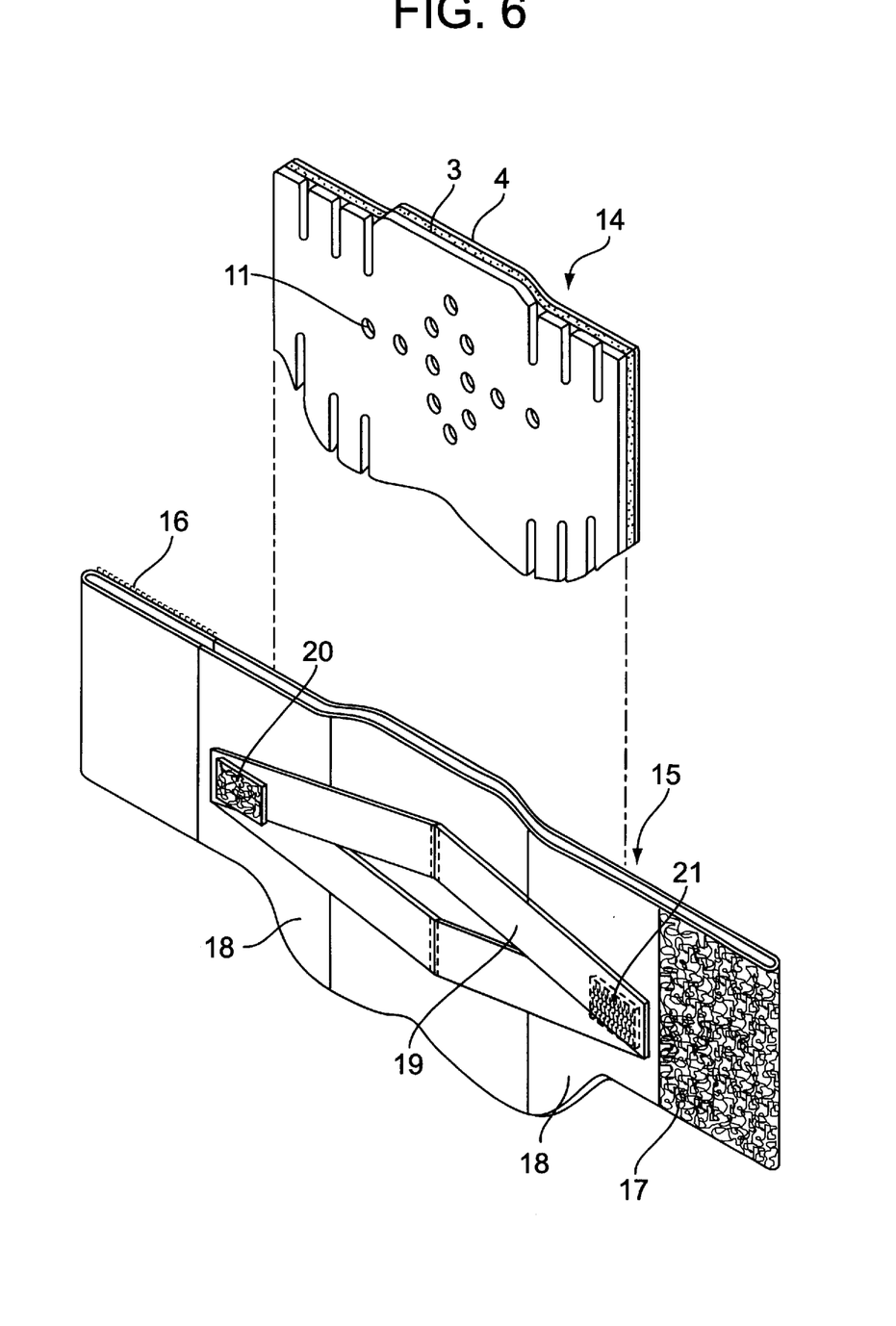
FIG. 6 is an exploded rear perspective view showing the configuration and construction of a splint for persons with a herniated disk according to another embodiment of this invention.

FIG. 6 shows the configuration and construction of a single splint for persons with a herniated disk according to a second embodiment of this invention. The splint according to the second embodiment includes an insert panel 14 which is formed of the same material as the panels 1 and 8 of the primary embodiment. The above insert panel 14 is covered with an outer cover 15 prior to sewing the edge of the cover 15. A wide hook strip 16 of a first VELCRO fastener is mounted to one side edge of the cover 15, while a wide rough strip 17 of the first VELCRO fastener is mounted to the other side edge of the cover 15. The cover 15 also includes an elastic cloth 18. The cloth 18 is mounted to the cover 15 at a position inside each VELCRO strip 16, 17. The above cloth 18 not only allows the splint to be free of any rumples when the splint is worn, it also provides elasticity to the splint. In addition, an elastic band 19 with a second VELCRO fastener is sewn on the central portion of the cover 15. Both strips 20 and 21 of the second VELCRO fastener are mounted to both ends of the band 19, respectively.

Figure 7:
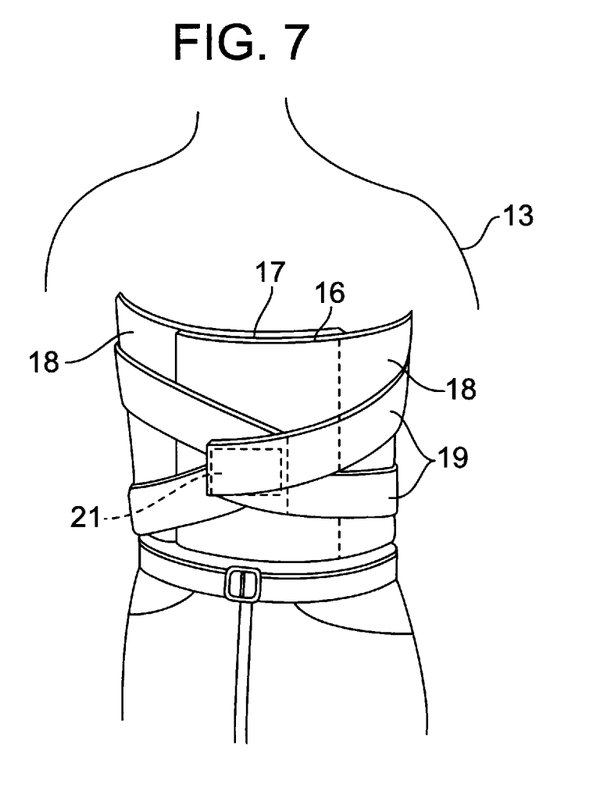
FIG. 7 is a front perspective view showing the operational effect of the splint of FIG. 6 put on a person with a herniated disk.

The above splint with the covered panel 14 is put on an affected part of the body of a person with a herniated disk in the manner as shown in FIG. 7. That is, the covered panel 14 is primarily wound on the affected part of the body prior to pressing the strips 16 and 17 of the first VELCRO fastener in order to stick them together on the front part of the patient. The splint put on the affected part of the body is thus primarily fastened. Thereafter, the elastic band 19 is stretched prior to sticking the strips 20 and 21 of the second VELCRO fastener together on the front part of the patient. The splint put on the affected part of the body is thus secondarily fastened.

The above cloth 18 has an appropriate elasticity and acts as a bending part of the splint when the splint is worn. Due to the elasticity of the cloth 18, the splint is free of any rumples when the splint is worn.

Figure 8:
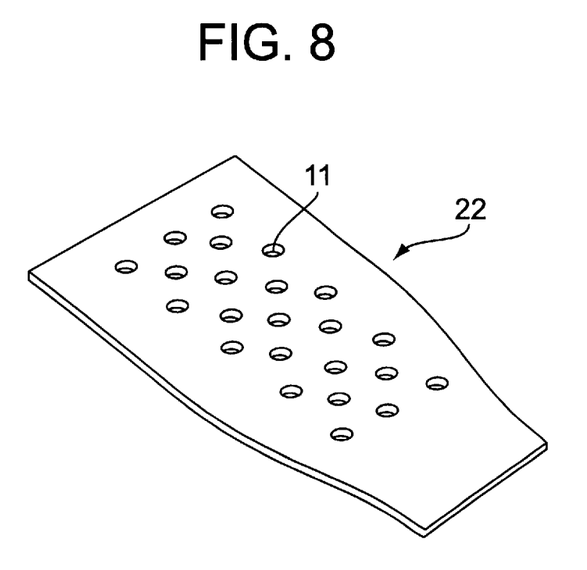
FIG. 8 is a perspective view of a typical arm splint for a person with a broken bone in one's arm.
Figure 9:
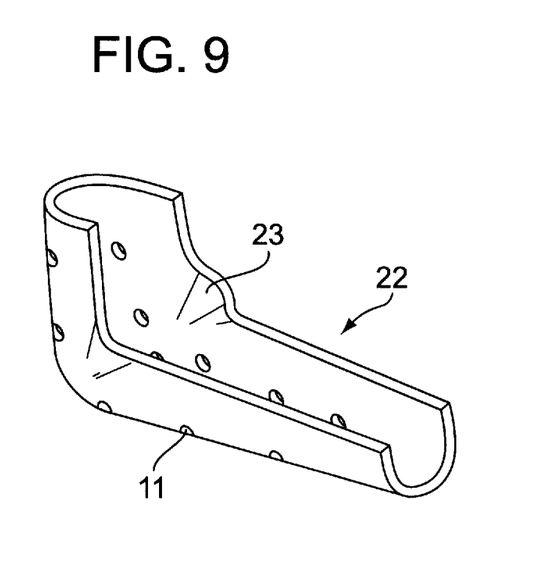
FIG. 9 is a perspective view of the typical splint of FIG. 8 shaped into a configuration agreeable to the contour of the affected arm.

FIGS. 8 and 9 show a typical arm splint which comprises a naked panel 22 formed of the above known material and which may be used for a person with a broken bone in one's arm.

As shown in FIG. 9, the typical arm splint has a problem in that the naked panel 22 is brought into direct contact with a patient's skin thus giving a bad sensation to the skin. In addition, rumples 23 are regrettably formed on the bending parts of the above splint.

Figure 10:
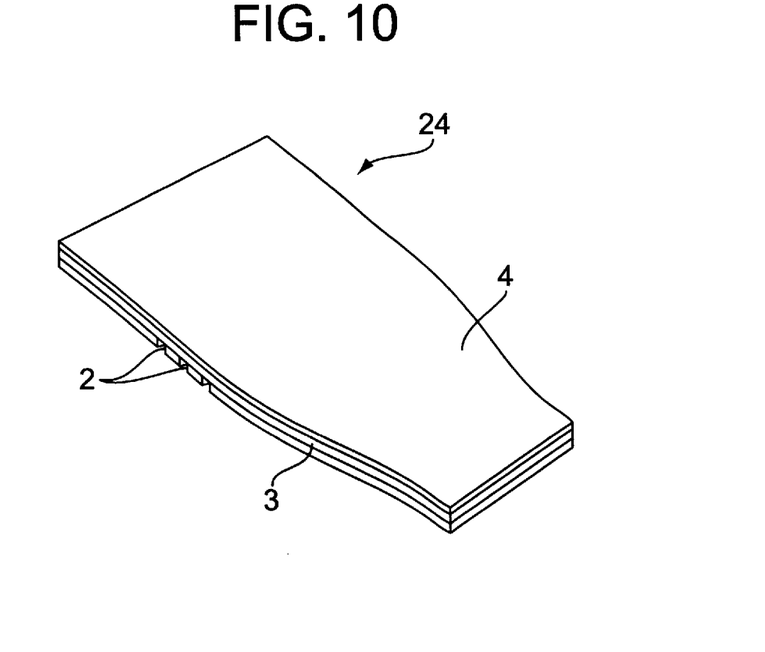
FIG. 10 is a perspective view of an arm splint for a person with a broken bone in one's arm in accordance with a further embodiment of the present invention.
Figure 11:
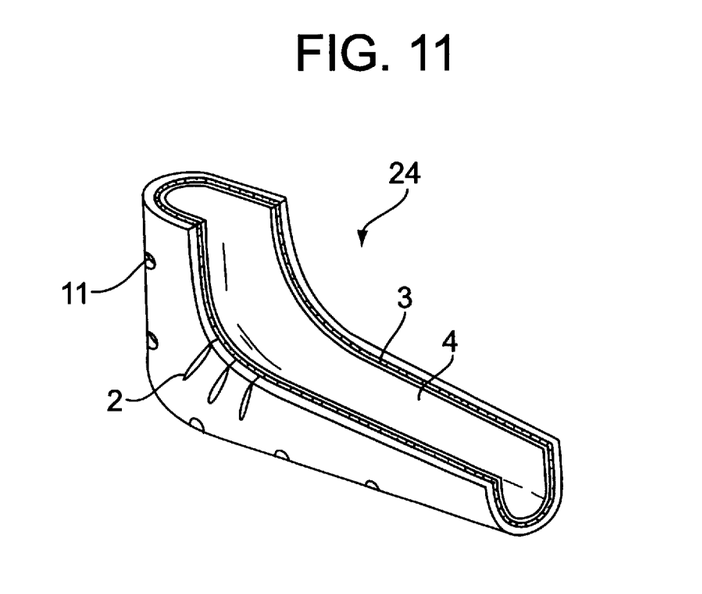
FIG. 11 is a perspective view of the arm splint of FIG. 10 shaped into a configuration agreeable to the contour of the affected arm.

FIGS. 10 and 11 are views corresponding to FIGS. 8 and 9, but showing an arm splint according to the invention. The arm splint of this invention comprises a panel 24 which is lined with a sponge 3 and a soft cloth 4, both having the same size as the panel 24, in the same manner as described above. A plurality of slits 2 are formed on the bending parts of the panel 24. The operational effect of the slits 2, sponge 3 and cloth 4 is the same as the splint of FIG. 1.

Figure 12:
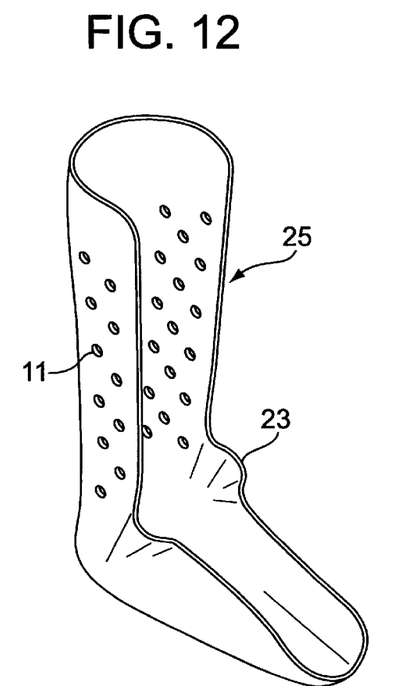
FIG. 12 is a perspective view of a typical leg splint shaped into a configuration agreeable to the contour of an affected leg with a broken bone.
Figure 13:
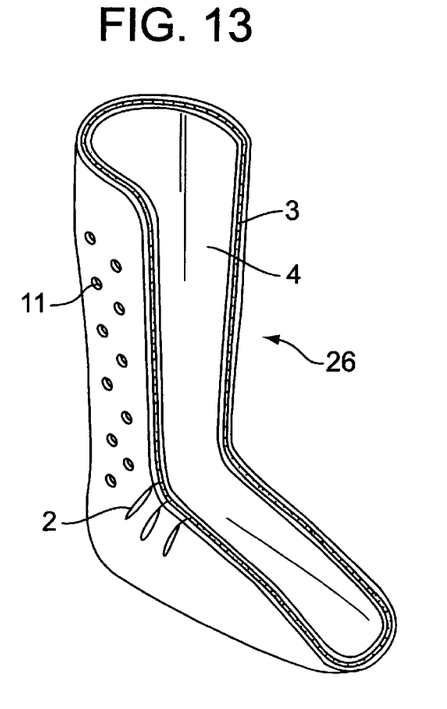
FIG. 13 is a perspective view of a leg splint shaped into a configuration agreeable to the contour of an affected leg with a broken bone in accordance with still another embodiment of the present invention.

FIGS. 12 and 13 are views comparing a typical leg splint 25 with a leg splint 26 of this invention. The general construction of the splint 26 is similar to that of the arm splint of FIGS. 10 and 11, so that the splint 26 yields the same result as described for the arm splint 24.

As described above, the present invention provides a structurally-improved splint used as medical supports for broken bones or herniated disks of persons so that the bones or disks stay in their particular positions while they heal. The splint of this invention is lined with a sponge and soft cloth thus giving a soft and delightful sensation to a patient's skin. The above splint also has a plurality of slits on its bending parts, thus being free of any rumples when put on an effected part of the body. The splint of this invention is also covered with an outer cover which allows the splint to be easily put on or removed from the affected part of the body.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A splint used as a support for a broken bone or herniated intervertebral disk so that the bone or disk stays in a particular position while it heals, comprising:

front and back panels comprising a material capable of being softened at a temperature in the range of about 70° C.–90° C., each of said panels being lined with both a sponge and a soft cloth and being covered with an outer cover and having a plurality of bending slits allowing each panel to be easily shaped into a configuration agreeable to the contour of an affected part of the body, said sponge being layered on the inside wall of each panel, and said cloth being layered on the sponge, said outer cover of said front panel having both a pocket and a hook and loop fastener strip, said outer cover of said back panel having a complementary hook and loop fastener strip, wherein said hook and loop fastener strips stick together when pressed thereby coupling said covered panels together into a jacket-type splint.

* * * * *